(12) United States Patent
Baym et al.

(10) Patent No.: US 10,777,304 B2
(45) Date of Patent: Sep. 15, 2020

(54) COMPRESSING, STORING AND SEARCHING SEQUENCE DATA

(71) Applicants: Michael H. Baym, Cambridge, MA (US); Bonnie Berger Leighton, Cambridge, MA (US); Po-Ru Loh, Cambridge, MA (US)

(72) Inventors: Michael H. Baym, Cambridge, MA (US); Bonnie Berger Leighton, Cambridge, MA (US); Po-Ru Loh, Cambridge, MA (US)

( * ) Notice: Subject to any disclaimer, the term of this patent is extended or adjusted under 35 U.S.C. 154(b) by 336 days.

(21) Appl. No.: 15/657,359

(22) Filed: Jul. 24, 2017

(65) Prior Publication Data

US 2017/0323052 A1 Nov. 9, 2017

Related U.S. Application Data

(62) Division of application No. 13/722,121, filed on Dec. 20, 2012, now Pat. No. 9,715,574.

(60) Provisional application No. 61/578,088, filed on Dec. 20, 2011.

(51) Int. Cl.
*G16B 50/00* (2019.01)
*H03M 7/30* (2006.01)

(52) U.S. Cl.
CPC .......... *G16B 50/00* (2019.02); *H03M 7/3062* (2013.01)

(58) Field of Classification Search
CPC ........ G16B 30/00; G16B 50/00; G16B 40/00; G16B 20/00; G16B 5/00; G16B 25/00; G16B 30/10; G16B 20/10; G16B 30/20; G16B 45/00; C12Q 2600/156; C12Q 1/6869; G06F 16/35; G06F 16/90344; G06F 16/9038; G06F 17/18; G06F 19/00; G06F 16/1744; G06F 11/0757; G06F 16/1752; G06F 16/2365; G06F 9/5016; G06F 16/22; G06F 16/244; G06F 16/2445; G06F 16/2453; G06F 16/24573; G06F 16/2458; G06F 16/901; G06F 16/9017; G06F 7/24; G06F 16/137; G06F 16/221; G06F 16/53; G06F 17/15; G06F 9/505; G06F 9/5055; G06N 7/005; G06N 10/00; G06N 20/00; G06N 20/10; G06N 5/022; G06N 3/04; G06N 3/10; G06K 9/6297; G06K 9/0014; G06K 9/6269; G06K 9/00147; G06K 9/4628; G06K 9/6289; G06K 9/72; H03M 7/3062; H03M 7/3068; H03M 7/30; H03M 7/3091; G16H 10/60; G16H 50/30; H04L 47/125; H04L 47/29; H04L 47/786; H04L 2209/30; H04L 2209/38; H04L 27/2613; H04L 43/02; H04L 63/0227; H04L 63/0245; H04L 63/0263; H04L 69/22; G05B 2219/35001; H04W 28/06
See application file for complete search history.

(56) References Cited

U.S. PATENT DOCUMENTS

| | | | | |
|---|---|---|---|---|
| 9,715,574 B2 * | 7/2017 | Baym | .................... | G16B 50/00 |
| 2008/0256070 A1 * | 10/2008 | Inglis | .................... | G16B 50/00 |
| 2012/0215463 A1 * | 8/2012 | Brodzik | ................ | G16B 30/00 |
| | | | | 702/20 |

* cited by examiner

*Primary Examiner* — Mary K Zeman
(74) *Attorney, Agent, or Firm* — David H. Judson

(57) ABSTRACT

The redundancy in genomic sequence data is exploited by compressing sequence data in such a way as to allow direct computation on the compressed data using methods that are referred to herein as "compressive" algorithms. This approach reduces the task of computing on many similar genomes to only slightly more than that of operating on just one. In this approach, the redundancy among genomes is translated into computational acceleration by storing genomes in a compressed format that respects the structure of similarities and differences important to analysis. Specifically, these differences are the nucleotide substitutions, insertions, deletions, and rearrangements introduced by evolution. Once such a compressed library has been created, analysis is performed on it in time proportional to its compressed size, rather than having to reconstruct the full data set every time one wishes to query it.

12 Claims, 5 Drawing Sheets

COMPRESSING, STORING AND SEARCHING SEQUENCE DATA

TECHNICAL FIELD

This subject matter relates generally to analysis of genomic data sets.

BACKGROUND OF THE RELATED ART

The past two decades have seen an exponential increase in genomic sequencing capabilities, outstripping advances in computing power. Extracting new insights from the datasets currently being generated will require not only faster computers; it will require smarter algorithms. Most genomes currently sequenced, however, are highly similar to ones already collected; thus, the amount of novel sequence information is growing much more slowly.

Successive generations of sequencing technology have exponentially increased the availability of genomic data. In the decade since the publication of the first draft of the human genome (a 10-year, $400 million effort), technologies have been developed that can sequence a human genome in one week for less than $10,000, and the 1000 Genomes Project is well on its way to building a library of over 2500 human genomes.

These leaps in sequencing technology promise to enable corresponding advances in biology and medicine, but they will require more efficient ways to store, access, and analyze large genomic data sets. Indeed, the scientific community is becoming aware of the fundamental challenges in analyzing such data. Difficulties with large data sets arise in a number of settings in which one analyzes genomic libraries, including finding sequences similar to a given query (e.g., from environmental or medical samples), or finding signatures of selection within large sets of closely related genomes.

Currently, the total amount of available genomic data is increasing approximately ten-fold every year, a rate much faster than Moore's Law for computational processing power. Any computational analysis, such as sequence search, that runs on the full genomic library (or even a constant fraction thereof) scales at least linearly in time with respect to the library size, and therefore effectively grows exponentially slower every year. To achieve sub-linear analysis, one must attempt to take advantage of redundancy inherent in the data. Intuitively, given two highly similar genomes, any analysis based on sequence similarity that is performed on one should have already done much of the work toward the same analysis on the other. While efficient algorithms such as the Basic Local Alignment and Search Tool (BLAST) have been developed for individual genomes, large genomic libraries have additional structure; they are highly redundant. For example, as human genomes differ on average by only 0.1%, one thousand human genomes contain less than twice the unique information of one genome. Thus, while individual genomes are not very compressible, theoretically collections of related genomes should be compressible.

Numerous algorithms exist for the compression of genomic datasets purely to reduce the space required for storage and transmission. Existing techniques, however, require decompression prior to computational analysis. Thus, while these techniques achieve a significant improvement in storage efficiency, they do not mitigate the computational bottleneck: in order to perform analysis, the original uncompressed data set must be reconstructed.

There have also been efforts to accelerate exact search via indexing techniques. While mapping short re-sequencing reads to a small number of genomes is already handled quite extensively by known algorithms, in the case of matching reads of unknown origin to a large database (e.g., in a medical or forensic context), known techniques have not proven satisfactory. Realizing acceleration becomes harder when one wishes to perform inexact search (e.g. BLAST and the Blast-Like Alignment Tool (BLAT)). To use compression effectively to accelerate inexact search requires a compression scheme that respects the metric on which similarity is scored.

There remains a need to provide new computational techniques that address these and other deficiencies in the known art.

BRIEF SUMMARY

According to this disclosure, the redundancy in sequence data (e.g., across genomes) is exploited by compressing sequence data in such a way as to allow direct computation on the compressed data using methods that are referred to herein as "compressive" algorithms. This approach reduces the task of computing on many similar genomes to only slightly more than that of operating on just one. In this approach, the redundancy among genomes is translated into computational acceleration by storing genomes in a compressed format that respects the structure of similarities and differences important to analysis. Specifically, these differences are the nucleotide substitutions, insertions, deletions, and rearrangements introduced by evolution. Once such a compressed library has been created, analysis is performed on it in time proportional to its compressed size, rather than having to reconstruct the full data set every time one wishes to query it.

The technique involves two (2) high level operations: pre-processing, and search. These operations may be carried out at different times, and using different resources. In the first (pre-processing) operation, a stream of sequence data is pre-processed to identify similarities. This pre-processing step generates a compressed database, together with a "links" table to the rest of the data. The size of the database is proportional to the amount of non-redundant data. In the second (search) operation, a coarse search is performed on the compressed data and then a more fine-grained search is performed only on the relevant portions of the database.

In particular, and according to a more specific embodiment, the basic compression operation begins by iterating through the sequence data, replacing sequence fragments sufficiently similar to previously-seen fragments with a link to the original sequence and a compact list of modifications. For a query step, a two-step variant of a search algorithm (e.g., BLAST, the Basic Local Alignment and Search Tool, or BLAT, the Blast-Like Alignment Tool)) is implemented. Thus, for example, in one embodiment the first step uses BLAST to search the unique data, i.e., the data not replaced by links during compression, with a relatively permissive hit threshold. The second step traces the links to determine potential hit regions in the full database and examines these potential hits with a stricter hit threshold (once again, using BLAST). Preferably, the initial "coarse" search runs on the compressed data without decompression, yielding a runtime proportional to the size of the compressed database. The second "fine" alignment is done by locally decompressing only the potential hit regions until either a hit is determined or can be ruled out.

Without limitation, the technique is useful to find sequences similar to a given query (e.g., in environmental genomics or genomic medicine), to find signatures of selection within large sets of closely related genomes, to find representation sets of genes for a collection of expression samples, and other purposes.

Among other advantages, the techniques described herein provide increased efficiency while maintaining similar search accuracy as compared to other known methods.

The foregoing has outlined some of the more pertinent features of the disclosed subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the subject matter and the advantages thereof, reference is now made to the following descriptions taken in conjunction with the accompanying drawings, in which.

DETAILED DESCRIPTION

For purposes of description and illustration, the techniques herein are described in the context of compressing genomic sequence data, although the same approach may be used to compress, store and search other large data sets wherein sequences of data therein are similar and the amount of novel sequence information (for sequences being added) is comparatively modest.

In addition, the examples below are implemented using versions of the widely-used BLAST and BLAT algorithms. This is not a limitation, however. As is well-known, BLAST and BLAT search a genomic database to identify sequences that are similar to a given sequence. As will be described, the techniques of this disclosure use such algorithms, but only in a second phase. In particular, the "compressive algorithm (s)" of this disclosure involve two (2) distinct phases: (i) compressing the database, and (ii) searching the compressed data. The compression phase can be realized using various schemes; a preferred approach is based on edit script compression, which is described below. The search phase is implemented using any existing search algorithm, such as BLAST and/or BLAT.

As will be described, to compress data (according to one embodiment), the technique stores only the differences between similar fragments (of sequence data), rather than the complete, highly redundant sequences themselves. This approach may be implemented by scanning the nucleotide database and identifying sequence fragments sufficiently similar to previously seen fragments. Once identified, these fragments are replaced with a link to the original sequence and compact list of differences. The initial data compression phase only needs to be done once, and the compressed database can be updated incrementally if new data are added. This approach substantially reduces the storage required for many genomes.

For the search phase, a two-step variant of BLAST may be used. First, the algorithm uses standard BLAST to search the unique data (i.e., data not replaced by links during compression) with a more permissive hit threshold (E value). Second, the algorithm traces links to determine potential hit regions in the full database and examines these potential hits with the original, stricter threshold. The initial "coarse" search runs on the compressed data without decompression, whereas the second "fine" alignment" is done by locally decompressing only the potential hit regions until either a hit is determined or the region is ruled out. In an alternative embodiment, BLAT is substituted for BLAST in the coarse search step, and BLAT's local alignment algorithm is used for the fine search.

Figure 1:
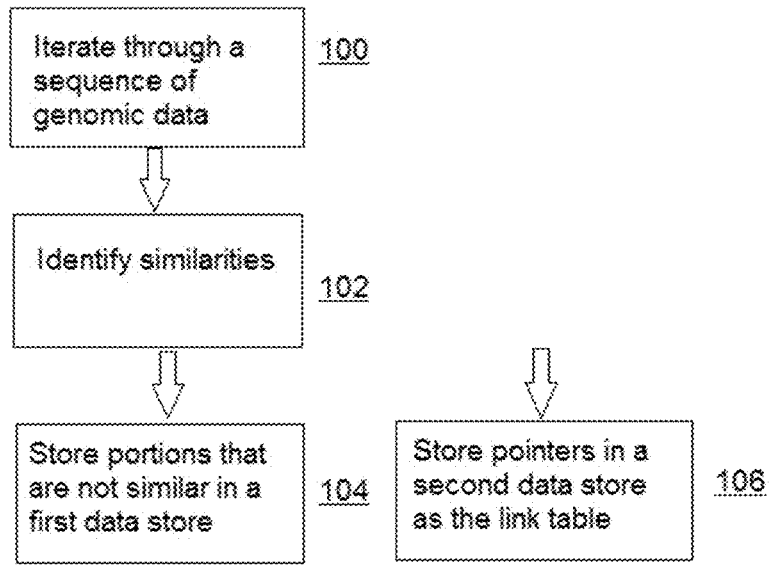
FIG. 1 is a process flow illustrating how a stream of genomic sequence data is pre-pre-processed according to this disclosure.

FIG. 1 is a process flow describing the basic pre-processing operation, which as noted above occurs in a first stage. This operation may be carried out in an off-line manner, or in computing entities that are distinct from those used during the search phase (described below). The particular compression approach is merely representative, but it is not intended to be limiting.

The routine begins at step 100 by iterating through a stream of genomic sequence data. During the iterating step, and responsive to a determination that a fragment of the genomic sequence is sufficiently similar to a previously-identified fragment, the fragment is then associated with a pointer together with a data string identifying one or more edits that, when applied to the previously-identified fragment, may be used to produce the fragment identified by the pointer. This is step 102. With respect to one or more portions of the stream that are not sufficiently similar to any previously-identified fragment, the one or more portions are stored in a first data store. This is step 104. At step 106, each pointer is stored in a second data store, which is sometimes referred to herein as the links table. Steps 104 and 106 may be carried out concurrently. In this approach, the pointer identifies a position of the fragment within the stream, and a position of the previously-identified fragment within the first data store. The pointer also includes an identifier associated with the data string. As will be described, the data string encodes one or more differences between the fragment and the previously-identified fragment, the differences being represented by one of: an insertion, a substitution, and a deletion.

Figure 2:
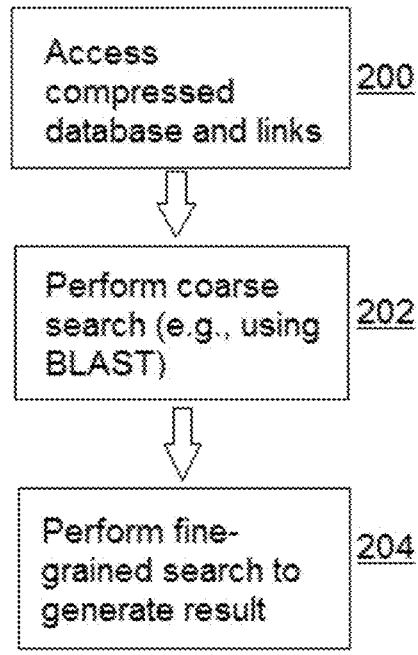
FIG. 2 is a process flow illustrating how the sequence data pre-processed according to FIG. 1 is searched in response to a query to generate an output result.

FIG. 2 illustrates the process flow describing the search operation, which is a second stage. As noted above, this operation may be carried out independently of the pre-processing operation, and by using distinct computing entities. This process begins where the pre-processing operation ends. Thus, it is assumed that a stream of sequence data has been pre-processed to identify similarities, and to generate the compressed database and the associated links table. The search operation comprises two sub-phases, a coarse search, followed by a fine-grained search. In particular, the compressed database and links table are accessed at step 200. At step 202, a coarse search (e.g., using an algorithm such as BLAST or BLAT) is performed on the compressed data. At step 204, a more fine-grained BLAST or BLAT search is then performed only on the relevant portions of the database. According to this approach, the first step 202 uses BLAST (or the like) to search the unique data, i.e., the data not replaced by links during compression, preferably with a more permissive hit threshold (E-value). The second step 204 traces the links to determine potential hit regions in the full database and examines these potential hits with an original (stricter) threshold. Preferably, the initial "coarse" search runs on the compressed data without decompression, yielding a runtime proportional to the size of the compressed database. The second "fine" alignment is done by locally decompressing only the potential hit regions until either a hit is determined or can be ruled out.

The particular searching operation described above is a representative approach (given the particular compression strategy used), but it is likewise not intended to be limiting.

Figure 3:
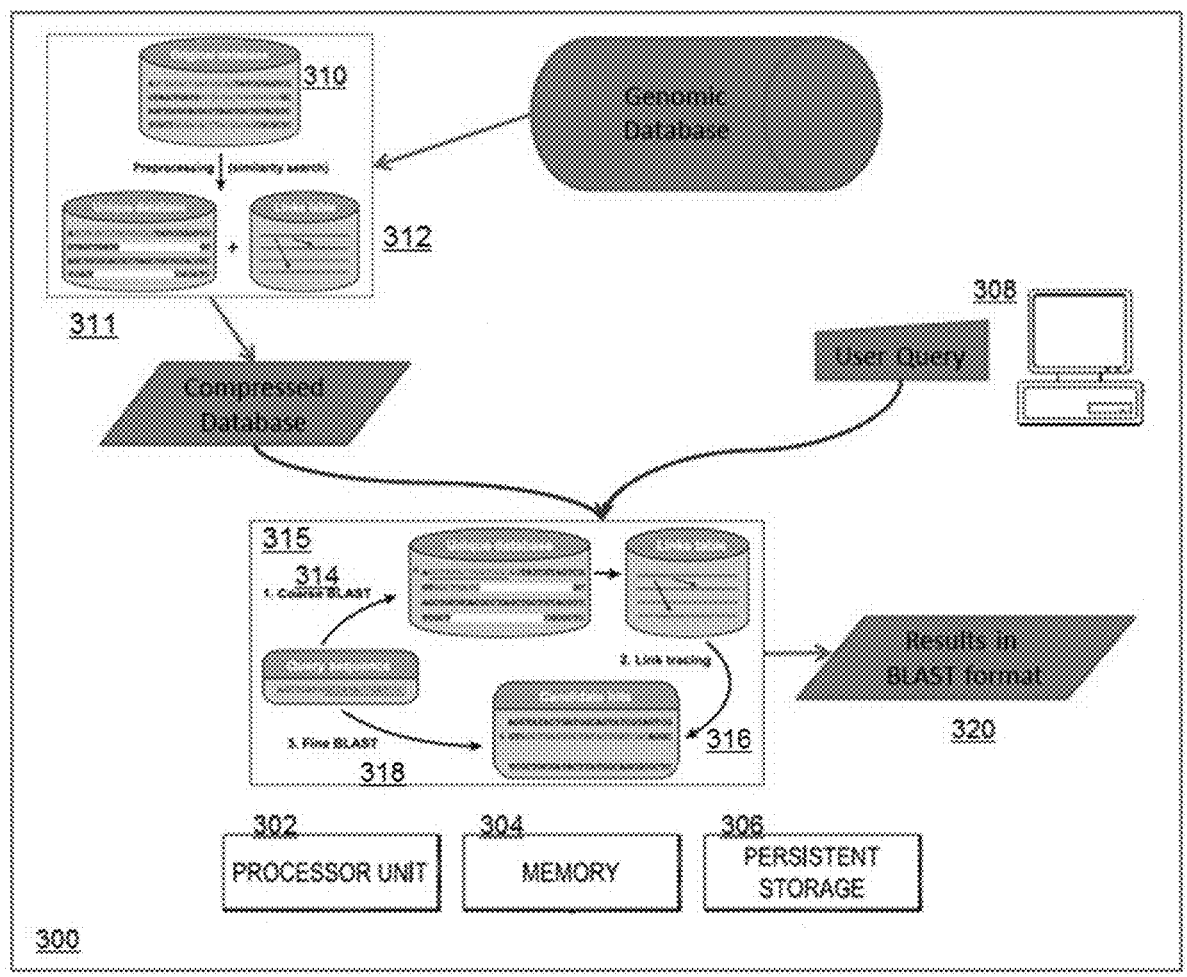
FIG. 3 illustrates an apparatus to compress, store and search sequence data according to this disclosure.

FIG. 3 illustrates these two stages, showing the end-to-end approach in more detail. For convenience of illustration, the operations are carried out in an apparatus 300 comprising a processor 302, memory 304, a data store 306, and a man-machine interface 308. Although a single computing entity is shown, this is not a limitation, as these computing elements may be distributed across multiple computers, disks, data stores, devices, interfaces, programs, processes, and the like. The various computing elements may be co-located or distributed across networks of any type and, as noted above, the illustrated operations may be carried out at different times.

During pre-processing, a scan through the genomic database 310 is performed to eliminate redundancy by identifying regions of his similarity and recording links to previously seen sequences. This results in unique database 311 and links table 312. The unique database 311 and the links table 314 are sometimes referred to herein as a "compressed database." In this example, the bolded sequence fragments in the figure match perfectly, aside from a few discrepancies (shown as italics). Thus, only the first occurrence appears in the unique database 311; information about the other two fragments (in this example) is then stored in the links table 314. A user initiates a search by entering a query in a user interface 308, which may be web-based. The interface also may be implemented in an automated or programmatic manner. During the search phase 315, a first search (e.g. using BLAST) is executed against unique database with relaxed E-value threshold. This is step 314. Additional candidate hits are recovered via the links table, which is step 316. At step 318, BLAST is executed against the candidate hits (as determined by the prior step) to select the final results 320. Here, the query (the underscore sequence) matches the second original sequence, but most of the second sequence does not appear in the unique database because of a similar region in the first sequence (bold). The coarse BLAST query thus hits only the first sequence; the second sequence is recovered as a candidate after checking the links table.

The following provides additional details regarding an implementation of the above-described methodology. Conceptually, and as seen in FIG. 3, the pre-processing phase views the original genomic database as an incoming stream of DNA, reading it base-by-base while building three main data structures: a unique database and links table (which are the output of the pre-processing phase), along with a table of seed 10-mer locations used internally. As will be described, the algorithm uses the latter table to rapidly identify seed matches, and then tries to extend them to longer alignments, similar to BLAT.

In one embodiment, the pre-processing algorithm (with arbitrary processing parameters specified solely for illustration) is implemented in suitable program code as follows:

1. Initialize unique database by copying first 10,000 bases of original database; set current base pointer to end of initial region. Initialize table of seed locations with all 10-mers occurring in the copied region. Initialize links table as empty.

2. A loop is then initiated. Move pointer forward one base. Look up 10-mer seed ending at current pointer position, along with its reverse complement, in table of seed locations.

3. For each seed match from the links table, attempt to extend match (as detailed in next subsection). If extended match of length at least 300 is found:
   (a) Augment links table with link to match.
   (b) Augment unique database with copy of original sequence data preceding alignment that is unaccounted for in unique database: specifically, bases from end of previous copied region (minus 100 bases) to start of current alignment (plus 100 bases).
   (c) Augment table of seed locations with locations (in the unique database) of all 10-mers occurring in the copied region; and
   (d) Move pointer to end of alignment (minus 100 bases) and go back to step 2.

4. If 10,000 bases have been processed with no alignments found, copy 10,000-base chunk to unique database, augment table of seed locations accordingly, move pointer to end of chunk (minus 100 bases), and go back to step 2. Otherwise, go back directly to step 2.

Because both matches stored in the links table and sequence data saved to the unique database are likely to consist of sequence fragments rather than complete entries from the original database, preferably, saved fragments are lengthened so that they overlap. In this embodiment, the algorithm saves an overlap of (e.g., 100) bases at transitions between adjacent fragments. The overlap represents an overhead cost per fragment; consequently, preferably the routine only uses alignments of length at least 300 during pre-processing.

The following provides additional details of alignment extension during pre-processing. As described above, during execution of the above algorithm, the routine must rapidly check if a 10-mer seed match extends to an alignment of length 300 or more, allowing only a limited amount of mutation in any chunk of consecutive bases. With this intuition, the algorithm attempts extension in each direction by hopping between matching 4-mers. The extension procedure preferably alternates between the following two steps:

1. Attempt un-gapped extension: scan forward along both sequences looking for the next 4-mer match assuming no gaps. When no 4-mer match is found within 10 bases or when there is less than 50% sequence identity between one 4-mer match and the next, move on to step 2.

2. Attempt gapped extension by local dynamic programming on the next (e.g., 25) bases of each sequence. In one approach, this is accomplished by extending the alignment by taking the path through the dynamic programming table containing the most matching bases. Along this path, identify matching 4-mers and extend the alignment to each successive 4-mer match that occurs within 10 bases of the previous and with at least 50% identity in between (as in step 1). If no acceptable 4-mer match is found, quit. Otherwise, restart step 1 after the last successful extension to a 4-mer match.

The final alignment is accepted as a match if it has length at least (e.g., 300) and sequence identity exceeding a user-specified threshold (70-90%) in every 100-base window of the alignment.

As seen in the above discussion, there are many constants used in the implementation. These are not intended to be limiting. In the embodiment, 10,000 bases is chosen as the maximum chunk size to be large enough to make the impact of link overhead minimal, while small enough to be able to decode hit regions within chunks without an excessive amount of decoding of extraneous regions. The 10,000-base limit also conveniently fit within a 2-byte integer. The overlap of consecutive fragments is selected to 100 bases so that a hit spanning consecutive fragments would likely be picked up as a hit to at least one of them; 100 bases was sufficient for this at typical search sensitivity thresholds for BLAST and BLAT. The lower-bounded usable fragment length (300 bases) was selected to reduce the impact of the overhead cost of overlaps. The alignment extension parameters were chosen to strike a reasonable balance between pre-processing speed and gap extension sensitivity. The basic idea is to run dynamic programming on a limited scale to detect gaps but give up when further alignment extension seems improbable, so as not to slow down the pre-processing. The parameters reported performed adequately for this purpose. Finally, the percentage identity requirement on 100-base windows of alignments represents a trade-off between search sensitivity and compression.

The following describes a known encoding technique, edit script compression, for use in the pre-processing. As described above, upon identifying a suitable alignment between a sequence fragment and a reference section of the unique database, the sequence data contained in the fragment is compressed by encoding the fragment as a pointer to the original sequence along with a string containing a series of edits that can be applied to the reference string to produce the aligned string. As high sequence identity between the aligned fragments can be assumed from the alignment step, edits can be treated efficiently as islands of difference surrounded by regions of exact matching. For each differing island, the routine stores a character indicating whether the modification is an insertion (i) or substitution/deletion (s). The routine then indicates the number of bases (encoded in octal) since a previous edit, and finally the sequence to insert or substitute. Note here that deletions are treated as a substitution of dashes for the reference bases. Given two sequences, the routine then generates an edit script. Preferably, each edit script is preceded by a 0 or 1, indicating whether the pair of aligned sequences is same-strand or reverse complemented, and also delineating the end of an edit script. On disk, preferably all the edits are concatenated into a single file. The full character set used by the edit scripts thus consists of 16 characters (0-7, A, C, G, T, N, -, i, and s) allowing a 4-bit-per-character encoding.

While the above encoding scheme is preferred, other known techniques may be used.

As noted, pointers are stored in the separate links table file. Each link pointer contains (e.g., 20) bytes of information: the start index of the aligned fragment within its originating sequence (4 bytes), the start index of the reference fragment within the unique database (4 bytes), the start index of the edit script within the scripts file (4 bytes), and the lengths of the two aligned sequences (2 bytes each). Some of this information can be deduced from the edit scripts; however, because a data structure containing this information for use during search is built, it is included in the links table files so as to truly be searching the compressed data without decompressing.

Algorithmically, the runtime of the pre-processing phase is in-between linear and quadratic (with an extremely small constant factor) in the database size depending on the amount of structure in the database. This slower step is run only once to create the searchable unique database plus links table; there is no need to run it for subsequent searches. The quadratic scaling arises on unstructured sequence data because at each position, the expected number of seed matches found roughly equals the current size of the unique database divided by the number of different seeds (in the 10-mer implementation, close to one million). When the original database contains significant regions of similarity, however, the runtime is closer to linear. In such situations, alignment extension (which takes time only linear in the alignment length) accounts for most of the bases processed; seed matches need only be looked up at the small fraction of positions between alignments. Thus, the runtime performance of pre-processing is highly data-dependent.

Additional details regarding the search phase are now described.

In one embodiment (using BLAST), the search phase applies the procedure below given a query and configurable coarse and final E-value thresholds:

1. "Coarse" BLAST. BLAST the query against the unique database to find hits passing the coarse E-value threshold.

2. Link-Tracing. For each hit, check the links table for other sequence segments that align to the hit region; recover original sequence segments corresponding to the hit. Extend these segments by a given number (e.g., 50) bases on each side (in the event the linked regions admit longer alignments to the query than the initial hit).

3. "Fine" BLAST. Re-BLAST against the expanded hits using the final E-value threshold.

The percent identity threshold (per 100-base window) that is used during pre-processing to decide whether an alignment qualifies as a link represents a trade-off between compression and accuracy. Relaxing the threshold allows greater database reduction, but it also increases the risk of overlooking alignments during search, due to greater differences between original sequences and their representatives. In general, accuracy improves while search speedup decreases as the similarity threshold is made stricter. The best parameter choice typically depends on the target application.

As noted above, BLAT may be used in place of BLAST during the search phase. In this alternative embodiment, the same pre-processing phase is performed to create a unique database and links table. BLAT is then called directly on the unique database for the coarse search. The output (e.g., in tab-delimited psl format) is then parsed; likely hit regions of the original library are then re-generated using the edit scripts from the links table. Finally, BLAT's internal ffFind( ) ("fuzzyfind") and scoreAli( ) routines are then called on these regions to match BLAT's alignment and scoring. BLAT by default uses a simple score threshold based on matches and mismatches between query and target as opposed to BLAST's E-value; thus, BLAT's minIdentity parameter may be used for coarse and fine search thresholds. For example, this parameter may have a default value of 90 for the final threshold and a value of 85 for the coarse threshold. These are example values only.

The BLAT embodiment has better performance (over the BLAST embodiment) when sequence chunks in the unique database are stored as separate entries, whereas BLAST performs better when all sequences in the unique database are concatenated into one large sequence. Additionally, BLAT's fuzzyfind algorithm (used for fine alignment) is more efficient when given hit regions are cropped closer to the aligning fragments; thus, hit regions are padded by only 10 bases during link-tracing.

Figure 4:
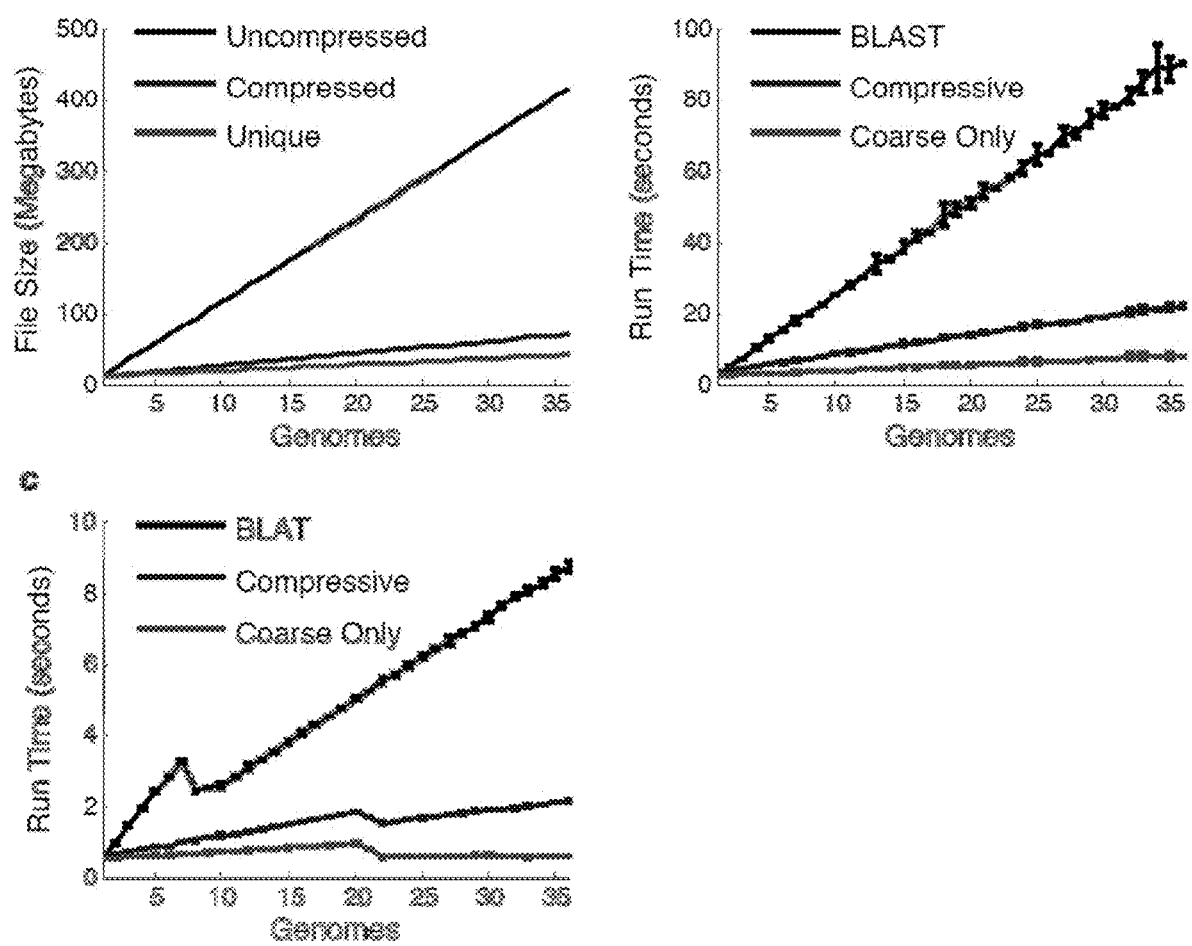
FIG. 4 illustrates the results of executing compressive algorithms on up to 36 yeast genomes using the described methodology.

FIG. 4 illustrates results of compression algorithms on up to 36 genomes. The first graph shows file sizes of the uncompressed, compressed with links and edits, and unique sequence data sets with default parameters. The second graph illustrates respective runtimes of BLAST, compressive BLAST and the coarse search step of compressive BLAST on the unique data ("coarse only"). The compression algorithm runtime was on a set of 10,000 simulated queries. For queries that generated few hits, the coarse search time provides a lower bound on search time. The third graph shows runtimes for BLAT, compressive BLAT and the coarse search step on the unique data ("coarse only") for 10,000 queries. BLAST and BLAT were both run with default parameters. The data displayed in these graphs represents differences between searches with 10,000 and 20,000 queries so as to remove any bias introduced by database construction time in BLAT.

Figure 5:
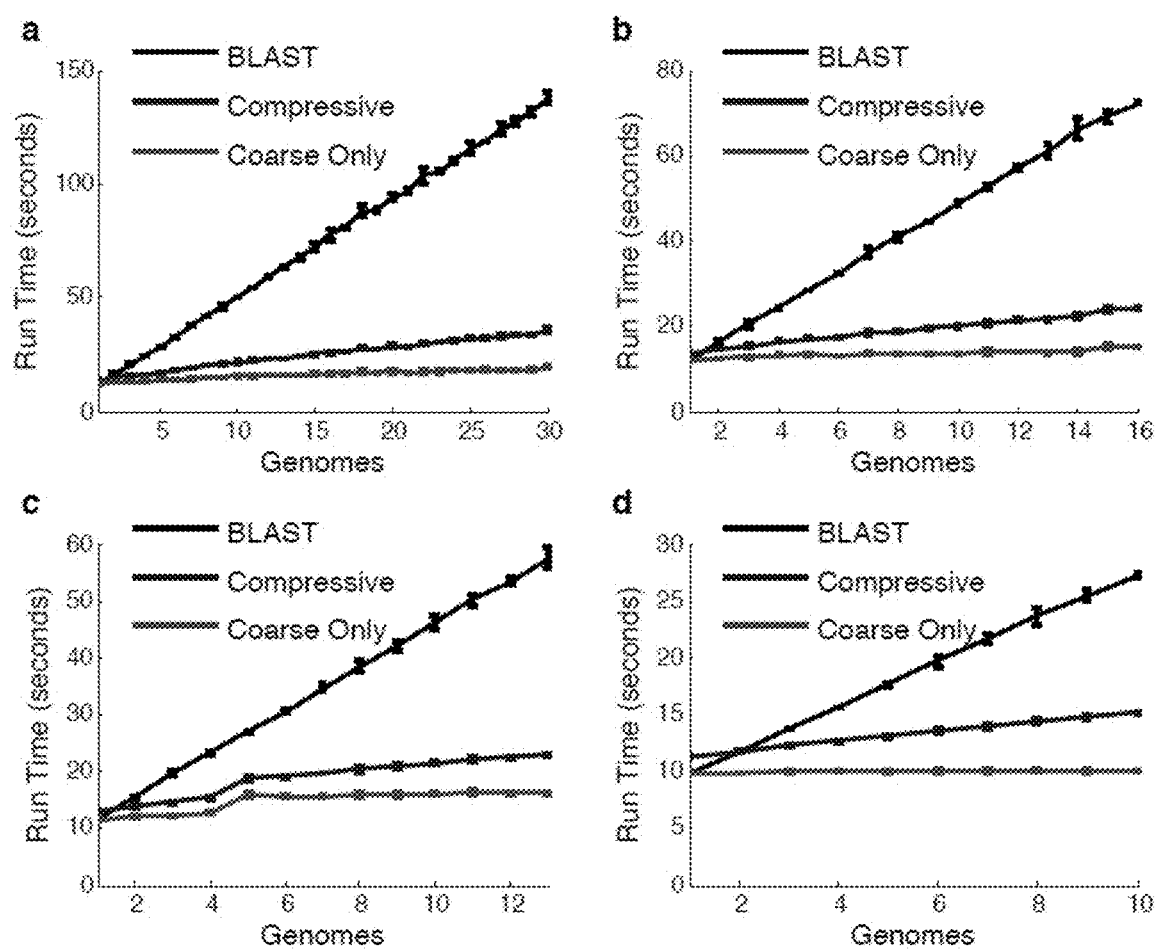
FIG. 5 illustrates performance of compressive BLAST on search sets derived from all five libraries of microbial sequences (four bacteria and yeast)

FIG. 5 illustrates performance of compressive BLAST on search sets derived from all five libraries of microbial sequences (four bacteria and yeast). The parameters are the same (default) as above and the graphs represent (a) *Escherichia*, (b) *Salmonella*, (c) *Yersinia*, and (d) *Brucella*.

Figure 6:
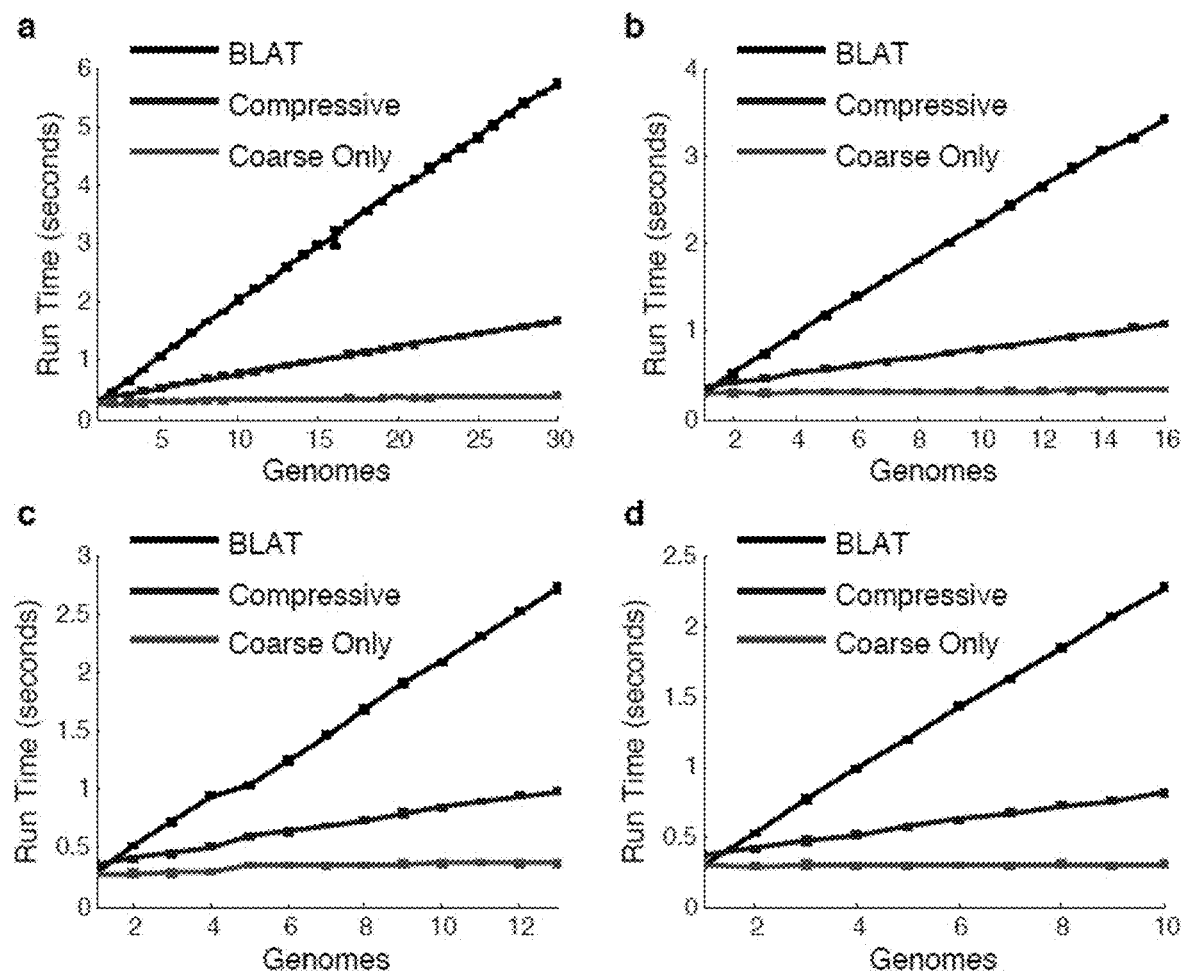
FIG. 6 illustrates performance of compressive BLAT on search sets derived from the microbial sequences (four bacteria and yeast).

FIG. 6 illustrates performance of compressive BLAT on all on search sets derived from the same genus of microbial species. The parameters are the same (default) as above and the graphs represent (a) *Escherichia*, (b) *Salmonella*, (c) *Yersinia*, and (d) *Brucella*.

As noted above, the use of BLAST or BLAT is merely exemplary and should not be taken to limit the subject matter. BLAST is chosen as a primary demonstration because it is widely used and also the primary means by which many other algorithms query large genomic datasets; thus, the improvement to BLAST provided by the compressive algorithm techniques of this disclosure will yield improvements in a range of analyses on large genomic datasets. The compressive architecture for sequence search described herein may be used with any algorithm that is based on sequence similarity.

The compressive algorithm techniques have many advantages. They exploit redundancy by compressing sequence data in such a way as to allow direct computation on that data. This approach significantly reduces the task of computing on many similar genomes to only slightly more than that of operating on just one. Moreover, its relative advantage over existing algorithms will grow with the accumulation of future genomic data. Compressive genomics according to the methodology herein will enable biologists to keep pace with current data. Moreover, the approach herein scales sub-linearly with the size of the data (i.e., those that reduce the effective size or do not operate on redundant data). Further, compressive genomic algorithms such as described may be implemented in distributed and multi-processor architectures. In the algorithms described, queries can be parallelized (as an example) by dividing the compressed library and link table among nodes, although the exact gains from doing so will be data-dependent, a function of the topology of the link graph on the uncompressed database.

The approach may be used on relatively small datasets and extended to a larger corpus of sequencing data (perhaps several terabytes of raw data), which are not addressable currently by non-compressive approaches of the prior art.

As noted above, the techniques herein are not limited to use with a particular compression strategy, or even a particular search strategy. The replace-by-links-based compression strategy is useful, but other types of compression may be implemented. For example, the compression may be performed in a hierarchal manner by linking to a sequence which itself has links to other sequences. Similarly, the search phrase does not need to be only two steps, but rather could be a series of iterated (finer and finer) searches. Further, depending on the purpose, the "fine" phase may be an even less-accurate search method, a different method than the coarse search, or even omitted entirely.

A skilled person also will recognize that the techniques herein may be extended to provide additional benefits. Thus, for example, when building the database, the step of adding data does not need to be done simply by running through the entire database each time a new sequence is to be added. Rather, the same iterative search techniques described herein for searching the compressed database can be used to add new elements.

As used herein, the term "sequence" as it relates to "genomic sequence data" should be construed to mean an individual sequence, a sequence of sequences (a meta-sequence), or the like.

The techniques herein are not limited for use to compress, store and search genomic sequence data but may be used for any type of data that comprises a data sequence, whether that data is received or otherwise obtained as a stream, in bulk, or otherwise.

The techniques may be practiced within a single computing entity, across multiple data centers, using cloud compute infrastructure, or the like.

The techniques provide the capability to perform matching reads of unknown origin to a large database (e.g., in a medical or forensic context). Indeed, realizing acceleration becomes harder when one wishes to perform inexact search (e.g. BLAST and the Blast-Like Alignment Tool (BLAT)). To use compression effectively to accelerate inexact search requires a compression scheme that respects the metric on which similarity is scored. The techniques herein provide such advantages.

The references to BLAST or BLAT are not intended to be limiting, as any variant of those algorithms, or any other sequence search procedure, may be utilized in the methodology.

Compressive algorithms for genomics as described herein have the great advantage of getting proportionately faster with the size of the available data. While the compression schemes for BLAST and BLAT that are presented yield an increase in computational speed, and more importantly in scaling, they are only a first step. Many enhancements are possible; for example, hierarchical compression structures, which respect the phylogeny underlying a set of sequences, can be expected to admit additional long-term performance gains. Moreover, analyses of such compressive structures presumably will lead to insights of their own. As sequencing technologies continue to improve, the compressive genomic paradigm will become critical to fully realizing the potential of large-scale genomics.

As described above, the techniques described herein are provided using a set of one or more computing-related entities (systems, machines, processes, programs, libraries, functions, or the like) that together facilitate or provide the described functionality described above. In a typical implementation, a representative machine on which the software executes comprises commodity hardware, an operating system, an application runtime environment, and a set of applications or processes and associated data, that provide the functionality of a given system or subsystem. As described, the functionality may be implemented in a stand-alone machine, or across a distributed set of machines. The functionality (either the pre-processing or searching, or both) may be provided as a service.

As described above, one or more functions may be implemented in a cloud-based architecture. As is well-known, cloud computing is a model of service delivery for enabling on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. Available services models that may be leveraged in whole or in part include: Software as a Service (SaaS) (the provider's applications running on cloud infrastructure); Platform as a service (PaaS) (the customer deploys applications that may be created using provider tools onto the cloud infrastructure); Infrastructure as a Service (IaaS) (customer provisions its own processing, storage, networks and other computing resources and can deploy and run operating systems and applications).

The platform may comprise co-located hardware and software resources, or resources that are physically, logically, virtually and/or geographically distinct.

Communication networks used to communicate to and from the platform services may be packet-based, non-packet based, and secure or non-secure, or some combination thereof.

In one example, but non-limiting embodiment, the techniques herein may be implemented in a symmetric multi-processing (SMP) computing environment. SMP architecture typically comprises a multiprocessor computer hardware architecture where two or more identical processors are connected to a single shared main memory and are controlled by a single operating system (OS) instance. In the case of multi-core processors, the SMP architecture applies to the cores, treating them as separate processors. An alternative approach uses grid computing, using a federation of computer resources from multiple administrative domains.

More generally, the disclosed method (or any step therein) may be implemented in a computer that includes a processor and program instructions (or their equivalent logic) executable by the processor to provide the described calculations required by the algorithm. One example embodiment is a computer program product comprising a non-transitory computer-readable storage medium on which processor-executable instructions are encoded for performing the various methods.

While the above describes a particular order of operations performed by certain embodiments of the disclosed, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

While given components of the disclosed method and system have been described separately, one of ordinary skill will appreciate that some of the functions may be combined or shared in given instructions, program sequences, code portions, and the like.

What we claim is as follows:

1. A method, executed in one or more computing entities, comprising:
    compressing an original data sequence into a data structure having first and second portions, wherein compressing comprises the following sub-steps:
        analyzing the original data sequence to determine whether a sequence fragment is similar to a previously-identified fragment;
        upon determining that the sequence fragment is similar, associating the sequence fragment with a pointer, together with a compact list identifying at least one edit that, when applied to the previously-identified fragment, produces the sequence fragment identified by the pointer;
        storing each pointer in the second portion; and
        storing in the first portion each segment of the original data sequence that is not similar to any previously-identified fragment; and
    in response to a query, searching the first and second portions of the data structure, in lieu of the original data sequence, to identify a portion of the original sequence data, wherein searching comprises:
        searching the first portion to locate one or more first hits passing a first, coarse threshold;
        for each first hit, examining the second portion to identify other segments of the original data sequence that potentially align to the first hit;
        for each such other segment of the original data sequence that potentially aligns to the first hit, recovering an actual segment from the original data sequence; and
        searching each actual segment so recovered to locate one or more second hits passing a second, fine-grained threshold;
    wherein searching using the first, coarse threshold and the second, fine-grained threshold and recovering one or more segments against which the second, fine-grained threshold is applied enables response to the query without having to decompress information in the first portion prior to analysis, thereby yielding a search runtime proportional to a size of the first portion to facilitate efficient information retrieval of the original data sequence.

2. The method as described in claim 1 wherein the original data sequence is a genomic sequence.

3. The method as described in claim 1 wherein the search of the data structure is carried out using one of: BLAST, and BLAT.

4. The method as described in claim 1 wherein the compressing step is executed to trade-off execution speed against an amount of data stored in the first portion of the data structure.

5. The method as described in claim 1 wherein the pointer identifies a position of the sequence fragment within the original data sequence, and a position of the previously-identified fragment within the first portion.

6. The method as described in claim 5 wherein the pointer also includes an identifier associated with the compact list.

7. The method as described in claim 6 wherein the compact list encodes one or more differences between the sequence fragment and the previously-identified fragment, the differences being represented by one of: an insertion, a substitution, and a deletion.

8. The method as described in claim 1 wherein compressing is carried out as a pre-processing step prior to searching.

9. The method as described in claim 1 wherein compressing is carried out just once, and searching is thereafter carried out against the first and second portions over multiple queries.

10. The method as described in claim 2 wherein analyzing comprises reading the genomic sequence DNA base-by-DNA base.

11. The method described in claim 1 wherein determining whether a sequence fragment of the original data sequence is similar to a previously-identified fragment analyzes an extension of the sequence fragment.

12. The method as described in claim 1 further including partitioning the first portion and the second portion across multiple computing entities, and wherein the query is parallelized.

* * * * *